United States Patent [19]

Lahoda et al.

[11] Patent Number: 5,266,494
[45] Date of Patent: Nov. 30, 1993

[54] BENCH SCALE TREATABILITY METHOD FOR EVALUATION OF SOIL WASHING

[75] Inventors: Edward J. Lahoda, Edgewood Borough; David C. Grant, Gibsonia, both of Pa.

[73] Assignee: Westinghouse Electric Corp., Pittsburgh, Pa.

[21] Appl. No.: 648,674

[22] Filed: Jan. 31, 1991

[51] Int. Cl.$^5$ .............................................. G21F 9/00
[52] U.S. Cl. ......................................... 436/57; 436/60; 436/177; 134/10; 134/25.1; 134/26; 252/626; 252/625
[58] Field of Search ................... 436/57, 60, 177, 178; 134/10, 25.1, 26, 29; 423/DIG. 20; 252/626, 625

[56] References Cited

U.S. PATENT DOCUMENTS

| | | | |
|---|---|---|---|
| 4,606,774 | 8/1986 | Morris | 134/10 |
| 4,783,253 | 11/1988 | Ayres et al. | 209/2 |
| 4,783,263 | 11/1988 | Trost et al. | 210/638 |
| 4,841,998 | 6/1989 | Bruya | 134/10 |
| 5,019,175 | 5/1991 | Rogers et al. | 134/42 |
| 5,056,541 | 10/1991 | Schade et al. | 134/25.1 |
| 5,128,068 | 7/1992 | Lahoda et al. | 252/626 |
| 5,133,901 | 7/1992 | Peterson et al. | 252/626 |

OTHER PUBLICATIONS

Assink, J. W., *Contaminated Soil*, pp. 655-667, 1986.
Werther, et al., *Contaminated Soil*, pp. 887-889, 1986.

Primary Examiner—James C. Housel
Assistant Examiner—Long V. Le

[57] ABSTRACT

A process for determining the suitability of soil washing for various types of soils, sludges and other solids is disclosed. The process may be applied to relatively small soil samples which have been contaminated in order to determine the suitability and economics for treating the tested soil using a full-scale soil washing process. The process involves the steps of identifying the contaminated particle size ranges contained in the soil sample, identifying an effective extractant for removing the contaminant of interest, and identifying an effective leachate treatment approach for the particular soil sample of interest.

9 Claims, 2 Drawing Sheets

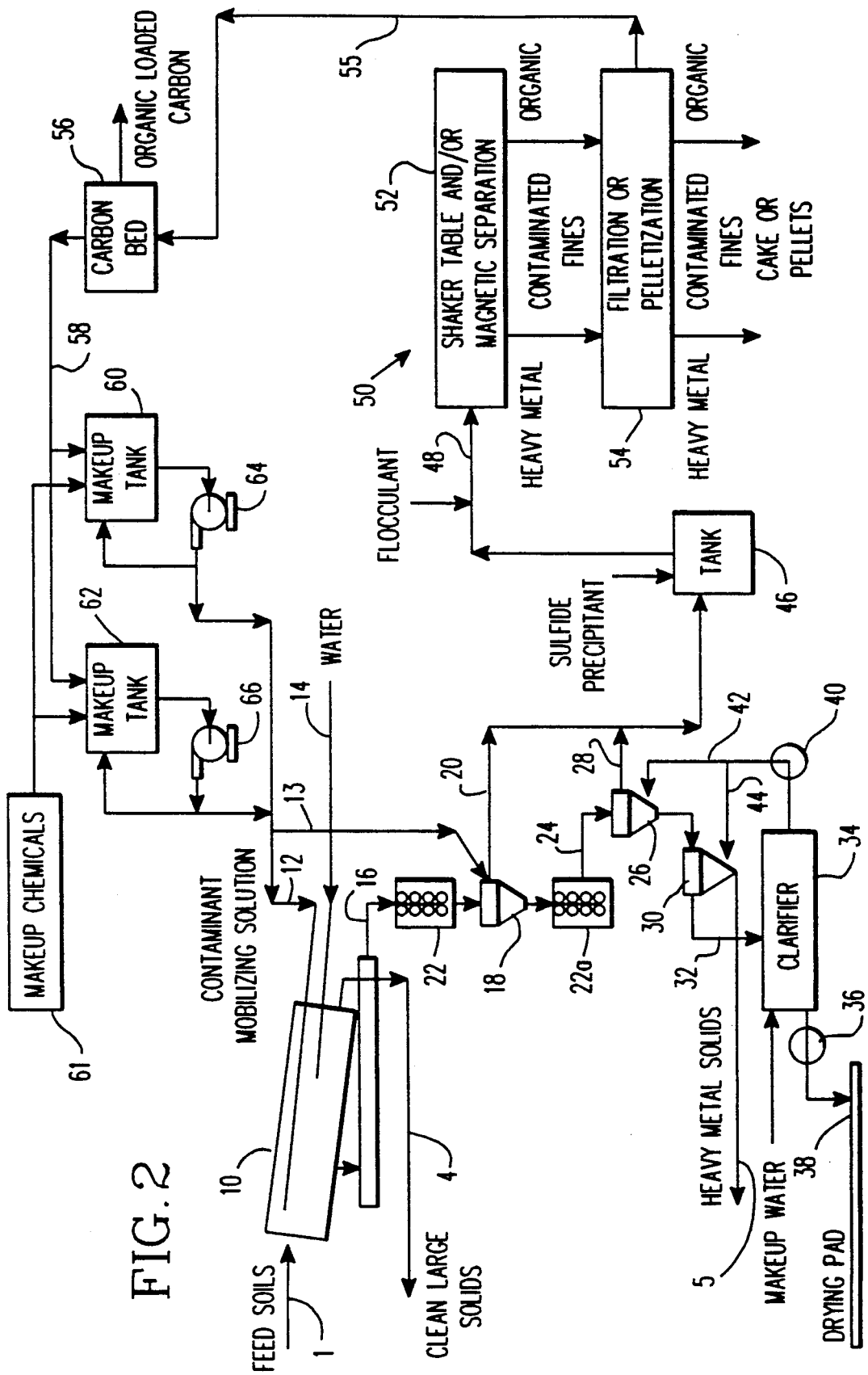

BENCH SCALE TREATABILITY METHOD FOR EVALUATION OF SOIL WASHING

FIELD OF THE INVENTION

This invention relates to a method and apparatus for cleaning particulate materials such as soils which are contaminated with a variety of contaminants such as heavy metals, radioactive compounds and organics, often in combination, through a combination of leaching, washing, attrition scrubbing, countercurrent flow size separation and density separation. This invention further relates to the recovery of such contaminates following removal from the soils, for additional processing, recycling or disposal. Most particularly this invention relates to a bench scale method of evaluating soil for contaminants and other conditions in order to determine the best approach for washing the soil.

BACKGROUND INFORMATION

Contaminated soil is becoming a more serious environmental problem every day. The contaminants can include heavy metals, such as for instance, copper, lead and mercury; radioactive species such as for example, radium, uranium and thorium; and organics such as for example, oils, polychlorinated biphenyls, (PCB's) flue soot and others. Various techniques have been developed to remove specific contaminants from soil. For instance, heavy metals are known to be found predominantly in the silt, humic or clay fraction of soil. Hence, they can be removed by size separation such as tiltable tables, concurrent flow in a mineral jig and chemical techniques, such as the use of leachates. The radioactive compounds when originating as a spill can be removed to a large extent by leaching. Since these compounds are often also present in the finer particles, the most severely contaminated fraction can also be removed by countercurrent flow size separation. Organics can be removed by washing with surfactants, thermal treatment or biological processes.

Special problems develop when the different types of contaminants are present in the same soil. Generally, biological or thermal processes are more effective for removing organics than washing, in the case of finer grain soils and clays. However, toxic inorganics such as lead or chromium ($+6$), if present, tend to deactivate biological systems due to their toxicity and aggravate air pollution problems endemic to thermal destruction process. In addition, thermal processes may mobilize contaminants that were otherwise fixed in the treated soil.

Radioactive contamination (e.g., uranium, thorium radium, etc.) can be removed by soil washing. Soil washing provides a means to process soils having multiple contaminants. The washed soil is compatible with subsequent biological or thermal treatment. Inorganic and radioactive compounds may be separated from organics for separate sale or disposal.

Many soil washing processes are presently available. Most use mine equipment to provide intimate soil/extractant contact. U.S. Pat. No. 4,783,253 discloses a process for separating radioactive contaminants from soil using a concurrent flow of water to float away lighter uncontaminated particles from heavy contaminated particles. The slurry of lighter particles is dewatered using a spiral classifier, centrifuge, filter or the like. U.S. Pat. No. 4,783,263 is directed to a process for removing toxic or hazardous substances, in particular organics, from soils and the like by converting the material to a slurry, adding surfactants and/or alkaline agents, and concentrating the toxic substance in the liquid phase preferably with a modifier in a froth flotation cell.

Some of the limitations of the currently used processes are that they are optimized for removing only one type of contaminant or for cleaning only one type of soil, they are geared to cleaning the larger particles while concentrating the fines in a fraction for later disposal, and they often use filtration for water removal which is a capital intensive operation with high operating costs.

Once the contaminants have been removed from the soil or other particulate material they must in turn be recovered for further processing, such as mining and/or smelting in the case of heavy metals, or disposal, for example, through mixing with a fixative material such as concrete. The ability to recover contaminants from the cleaning system is to a large extent dependent upon the method by which the contaminants were removed from the soil in the first instance. Mineral extraction in general and soil washing in particular often require the oxidation of the metals and sometimes the organic fraction of the soil for the removal of the metals. Radioactive metals are also included with heavy metals requiring oxidation, since most radioactive materials are also heavy metals, such as uranium, thorium or radium.

Some typical oxidants for heavy metal removal include nitric acid, sodium hypochlorite and calcium hypochlorite. However, the use of nitric acid is generally not practical due to the fact that nitric acid is nonselective in its action, dissolving the rock matrix as well as oxidizing and dissolving the metal of interest, it is expensive, and results in nitrate-laden waste liquors which can present environmental hazards unless treated. Sodium hypochlorite is expensive to use because commercial solutions are supplied as a 15% liquid which increases the freight costs. Calcium hypochlorite introduces large amounts of calcium ion into the leachate solution when used in quantities sufficient to oxidize the metal, and the calcium ions can then precipitate if carbonate bleach liquors are used or if the leachate solution is left standing in contact with air. This calcium carbonate precipitate is difficult to handle and can clog processing equipment. In addition, if common soaps are used to remove organics, the high calcium ion content tends to precipitate some of the soap which requires use of additional soap.

In addition to the above problems, frequently, it is not immediately clear which of the several possible soil washing techniques, or combinations thereof, should be used for a soil of particular interest. Even if the precise nature of contamination is known (and it may not be) the most efficient method of removing that contaminant or contaminants may depend on a host of variables and trial-and-error solutions. Attempting to make a determination of the economics of particular processing methods and parameters in the field is impractical, and would require shifting and replacing relatively large pieces of equipment, refitting pumps and piping, etc. until the best soil washing approach is determined for each particular site. Furthermore, field equipment often requires large batches of soil to operate effectively, further increasing the inefficiency of determining an optimal washing method for the particular soil.

There is a need therefore for an improved process and apparatus for treating particulate materials, such as soil and the like, contaminated with a mixture of wastes such as radioactive materials, organics and heavy metals.

There is a further need for such a process and apparatus which separates organic and inorganic contaminants thereby allowing for optimum disposal routes or post treatment strategies to be used on the concentrated contaminated fractions.

There is also a need for such a process and apparatus which produces a high solids content fines stream.

There is yet another need for such a process and apparatus which is not capital intensive, is economical to operate and can be made portable for on-site treatment.

There is a further need for a system that can effectively recover the contaminants once they have been removed from the soil, requiring a minimal amount of equipment, chemicals, and being portable to the job site, which further allows for the processing of recovered contaminants, such as metals, through mining and/or smelting operations, and allows for effective leach-resistant fixation of contaminants which are to be disposed.

There is also a need for a scaled-down soil washing evaluation system which may be run on relatively small batches of contaminated soil and which quickly and accurately provides optimal soil washing parameters for the particular contaminated particulate matter being evaluated, be it soil, sludge or other solids.

OBJECTS OF THE INVENTION

It is an object of the invention to provide a bench or small scale process for treating contaminated soils which contain organic and/or inorganic contaminants and is able to remove such contaminants from a few pounds or less of soil sample.

It is a further object to provide a process which evaluates the distribution of contaminants in the soil of interest.

It is yet another object of the invention to provide a process which evaluates the extraction efficiency of a variety of extractants while modeling the soil washing process of interest.

It is still a further object of the invention to provide a process which evaluates the effectiveness of the various leachate treatment steps.

It is another object of the invention to provide a process which determines the volumes and probable product recoveries and contaminant concentrations in those product streams.

It is a further object of the invention to determine the amount of extractants, acids, flocculent, and other chemicals needed for operation of any soil washing system.

These and other objects and advantages of the present invention will become more readily apparent as the following detailed description of the preferred embodiments proceeds.

SUMMARY OF THE INVENTION

According to the present invention, a method of characterizing contaminated soil in order to determine an effective treatment approach for removing contaminants from the soil is disclosed. The method comprises the steps of obtaining a representative contaminated soil sample from a site containing the contaminated soil; identifying particle size ranges for the contaminated soil by passing at least a portion of the representative contaminated soil sample through a series of particle size classifiers; identifying contaminants to be removed from the contaminated soil; identifying an effective soil washing extractant by passing at least a portion of the representative contaminated soil sample through a bench scale soil washing process adapted to substantially correspond to a full-scale soil washing process for the contaminated soil, the bench scale soil washing process being adapted for removing contaminants from contaminated soils having particle size ranges corresponding to the ranges identified in the previous step, the bench scale soil washing process including washing a known quantity of the representative soil sample with a first extractant, then repeating the bench scale soil washing process using at least one additional extractant (which may be a different concentration of the first extractant) and recovering and identifying at least one of the contaminants from the representative contaminated soil sample, in order to determine those soil washing conditions favoring extraction of the contaminant from the contaminated soil; and identifying a suitable leachate treatment process for treating at least one contaminant removed in the previous step from the representative contaminated soil sample.

In one preferred embodiment of the invention the particle size classifiers comprise a set of screens including a first screen and at least one additional screen arranged in order of decreasing screen size relative to the direction of passing the representative soil sample through the screens.

BRIEF DESCRIPTION OF THE DRAWINGS

FIG. 2 is a more detailed schematic representation of a typical soil washing flowsheet.

DETAILED DESCRIPTION OF THE PREFERRED EMBODIMENTS

Figure 1:
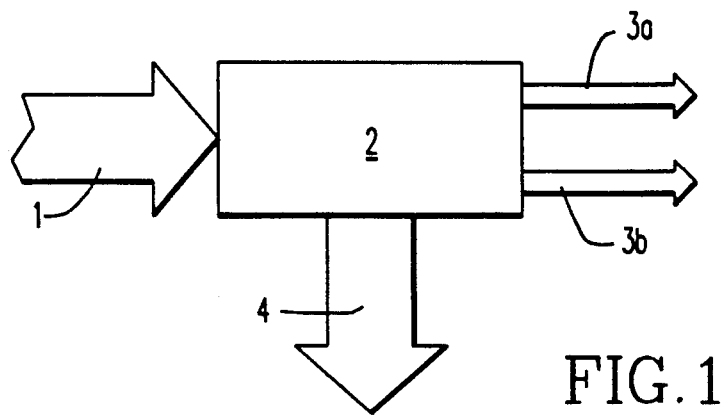
FIG. 1 is a schematic representation of a typical soil washing concept.

Referring to FIG. 1, a simplified schematic of a typical soil washing concept is illustrated, in which contaminated soil, generally 1, is transported through a soil washing system, generally 2, which may comprise chemical extraction or physical separation or combinations thereof, depending on the contaminant being removed from the soil. The contaminated concentrates or effluent removed from the soil washing system 2 can comprise one or two streams, a radioactive/heavy metal stream 3a and an organics stream 3b. The radioactive/heavy metal stream 3a is typically concentrated for disposal or processing as recovered metal ore feed. The organics are typically rendered more environmentally acceptable either through biotreatment or thermal degradation. The clean soil which is recovered 4 is typically returned to the site.

The process illustrated in FIG. 1 reduces the volume of contaminants and therefore the cost of remediating the contaminated site. The soil washing process is based upon commonly available mineral treatment processes for handling larger particles. Several of these soil washing processes have been successfully employed in Europe for several years for washing contaminated soils.

Examples include the clean-ups at HWZ Bodemsanering B.V. where 98% of the PNA's were removed. See "Extractive Methods for Soil Decontamination; A General Survey and Review of Operational Treatment Installations," J. W. Assink *Contaminated Soil*, First International TNO Conference on Contaminated Soil, Nov. 11-15, 1985, UTRECHT, the Netherlands, p. 655, incorporated by reference herein. As another example, at a clean-up in Hamburg, 90% of the heavy metal and organic contents were removed by simple size classification. See "Sand From Dredge Sludge—Development of Process for the Mechanical Treatment of Dredged Material", J. Werther, et al., First International TNO Conference on Contaminated Soil, Nov. 11-15, 1985 UTRECHT, the Netherlands, p. 887, incorporated by reference herein.

Referring to FIG. 2, a particular embodiment of a soil washing process is illustrated. This process is described in a copending U.S. patent application Ser. No. 529,092 now U.S. Pat. No. 5,128,068, Jul. 7, 1992, commonly owned by the asignee of the present invention. Initially, the excavated soil 1 is processed to remove large rocks and debris. This step is not shown in FIG. 2. The soil is then processed in a mechanical size separator 10 such as for instance a rotating drum or vibrating screen device to sort and prewash the feed soil with a contaminant mobilizing solution, provided through line 12. Large pieces of soil, for instance larger than 5 mm are washed with the contaminant mobilizing solution, rinsed with water supplied through line 14, checked for residual contaminants, and returned to the site as recovered soil. The contaminant mobilizing solution (or process stream) used to wash the soil will be dependent upon the contamination to be removed. For soluble contaminants, the solution will contain a leaching agent. Many suitable leaching agents are known and common leaching agents suitable for leaching radioactive compounds include for example potassium carbonate, sodium carbonate, acetic acid, sodium hypochloride, and others. Leaching agents for contaminants typically found in contaminated soils and the like are well known. For dispersible contaminants, the contaminant mobilizing solution contains a suitable surfactant. Again, suitable surfactants for dispersing contaminants such as oil, grease, polychlorinated biphenyls, etc., are also known. The contaminant mobilizing solution may contain various combinations of leaching agents and surfactants, again, depending on the contaminants in the soil to be cleaned.

The effluent of soil particles smaller than 5 mm. and contaminant mobilizing solution discharged from the mechanical separator 10 through line 16 is then processed in a countercurrent flow size separator such as the mineral jig 18. In the jig 18, additional contaminant mobilizing solution supplied through line 13 flows upwardly countercurrent to the effluent. The fines are carried upwardly with the upward flow of contaminant mobilizing solution to form a slurry which is discharged through a line 20. These fines typically include heavy metal particles. The velocity of the upward flow of contaminant containing solution in the mineral jig 18 is set to separate fines of a desired size, for example fines smaller than 60 microns in diameter. The slurry discharged in the line 20 includes, in addition to the fines, contaminant mobilizing solution which contains leached and dispersed metals and organics.

Heretofore, mineral jigs such as that disclosed in U.S. Pat. No. 4,873,253, have only been operated in a concurrent flow mode. We preferably operate the mineral jig 18 in a countercurrent flow mode. For such countercurrent flow operation, the jig can be operated with a stroke length of ½ to ¾ inch, a pulse frequency of 300 to 400 per minute, an upflow rate of contaminant mobilizing solution of 1 to 8 liters per minute, an underflow rate of 1 to 3 liters per minute, with one layer of balls 3/16 inch in diameter or greater to provide a soil under flow of 80 to 95 percent and soil over the top of 20 to 5 percent.

The intermediate sized particles between 5 mm and 60 microns in diameter, which are discharged from the bottom of the mineral jig 18, are abraded in an attrition scrubber 22a which dislodges mineral slime or fines from them. Another attrition scrubber 22 may precede the mineral jig 10. The intermediate sized particles and the dislodged fines discharged from the attrition scrubber 22a through line 24 are rinsed in a second countercurrent flow size separator such as the second mineral jig 26 operated in the manner discussed above in connection with jig 18. The countercurrent flow in the second mineral jig 26 is wash water which flows upwardly at a velocity again selected to separate the dislodged fines, typically of 60 microns in diameter and smaller. The slurry of fines and wash water is discharged through line 28.

The remaining intermediate sized particles discharged from the second mineral jig 26 are processed in a density separator such as a cross-current flow jig 30 to extract higher density heavy metal solid waste particles. The mineral jig 30, which is similar to the jigs 18 and 26 is operated in the cross-current flow mode with a stroke length of ⅛ to 3/16 inch, a pulse frequency of 100–400/min, a water upflow rate of 1 to 8 liters/min, one to three layers of balls less than 3/16 inch to provide soil over the top of 80 to 95 percent and a soil underflow of 20 to 5 percent. The cross-current flow carrying the intermediate sized soil particles is discharged through a line 32 into dewatering apparatus such as, for instance, a clarifier 34 or a hydroclone. Sludge from the clarifier 34 is pumped by a pump 36 onto a drying pad 38. The dried particles recovered from the drying pad are checked for cleanliness and returned to the site as additional cleaned soil. Water removed by the clarifier 34 is circulated by a pump 40 through a line 42 as the countercurrent wash water for the second mineral jig 26, and through line 44 as the cross-current flow for the density separator jig 30.

The two waste slurry streams in the lines 20 and 28 from the first and second mineral jigs 18 and 26, respectively, are discharged into precipitation equipment 46 to which is added a precipitant to precipitate the dissolved metals. A sulfide or other suitable agent can be used to precipitate the dissolved metals present in a particular contaminated soil. These precipitates and fine soil particles will be highly contaminated with organics and heavy metals. A flocculant, such as for example Nalco 7182, an anionic polymer that does not interfere with trace metal absorption and co-precipitation, supplied by the Nalco Chemical Company, Naperville, Ill., is added to the precipitates and fines conveyed from the precipitation equipment 46 through a line 48 to dewatering apparatus 50 which may include for instance Bardles-Mozley concentrator 52 which separate micron size particles of high specific gravity. Simultaneously, fine particles are washed by the high shear, orbital shaking of the table. Fine soil solution which is washed from the table is passed through high intensity matrix magnetic separators which remove micron sized particles coated with weakly paramagnetic hydroxides containing inorganic contaminants. Solids from the remaining solution are then separated from the stream by either filtration or flocculation settling and pelletizing in apparatus 54. The organically contaminated fractions can be further treated biologically, chemically or thermally and returned to the site.

Concentrated solids removed by the Bartles-Mozley concentrator 52 can be disposed of or sold as a concentrate. The filtrate is passed through the line 55 to an activated carbon bed 56 to remove all organics before being sent through line 58 for recycling. The recycled solution is discharged in the one of two contaminant containing solution makeup tanks 60 and 62 which is not currently being used to feed the process. Makeup chemicals 61 may be supplied and/or recycled to the makeup tanks 60 and 62. The contaminated activated carbon in the bed 56 can be thermally or chemically treated or buried. The recycled contaminant mobilizing solution is analyzed and an active component such as caustic or emulsifier are made up on a batch basis in the off-line makeup tank 60 or 62. Contaminant mobilizing solution from the active one of the tanks 60 and 62 is pumped by the pump 64 or 66, respectively, through the line 12 to the mechanical size separator 10 and through the line 13 to the first mineral jig 18.

Referring again to FIG. 2, excavated feed soil (representative contaminated soil sample) is first processed to remove large rocks and debris and yield a pre-washed feed soil 3 by processing the feed soil 16 in a rotating drum or vibrating screen 10 to prewash the feed soil 16 using extractant 12 and remove larger particles greater than a nominal one-inch in diameter. Large particles, 4, generally greater than 48 mesh, which are more likely to be uncontaminated, have been washed with a leach solution, rinsed with water and are returned to the site.

The remaining contaminated soil is then processed in one or more attrition scrubbers 22 followed by a mineral jig 18 which provides counter-current contact between soils less than 48 mesh and greater than 44 microns and the leach solution. The fines, generally less than 44 microns, are carried over with the wash solution which contains leached organics and metals, 20, 28. The contaminants are precipitated from this stream and removed using flocculation, for example by adding NaOH, and $Na_2SiO_3$. The washed soils less than 48 mesh and greater than 44 microns are then abraded in a second attrition scrubber 22a and rinsed in a second counter-current mineral jig 26, treated for removal of high specific gravity metal contaminants in a specific gravity separator 30, monitored and returned to the site. The fines and wash water go to the flocculation and dewatering system 50 for precipitation and removal.

One of the problems associated with remediating a contaminated site, regardless of the particular soil washing technique being used, is how to inexpensively determine whether or not the particular soil washing process is both a technically and economically feasible remediation approach.

We have found that it is possible to run a bench scale or reduced scale process on virtually any soil sample using only a few pounds of sample to determine the appropriate processing parameters for a full scale soil cleaning operation. The bench scale tests can be run in a small area, remotely if needed, which makes the invention suitable for use with hazardous or radioactive materials which must be treated with special care.

The essential steps of the process include first identifying the contaminated particle size ranges contained in the soil sample, followed by identifying an effective extractant for use in connection with the contaminants contained in that sample, followed by identification of an effective leachate treatment approach for use with respect to the particular soil and contaminants of the sample. Each of these three aspects to the process will now be discussed in greater detail.

Before engaging in the process of the present invention, it is necessary to first obtain a representative contaminated soil sample from the site of interest which contains contaminated soil for which cleaning is desired. In this regard, it may be preferable to obtain a number of samples from various locations at the site in order to establish that soil processing parameters and needs are consistent throughout the site. Every effort should be made to obtain a soil sample which fairly represents the characteristics of the contaminated soil contained in the site as a whole, in terms of particle size, contaminant contained in the soil, etc.

Once a representative contaminated soil sample is obtained from the site, according to the present invention it is necessary to evaluate that sample to determine the various particle size ranges making up the sample and the weight fraction of each range in that sample. Any suitable particle size classifying apparatus may be used for this function, although we have found sieves, preferably USA standard testing sieves meeting ASTM E-11 specifications to perform acceptably.

The sieves to be used in classifying the particle size ranges are identified by sieve size for example, Nos. 10, 20, 50, 100, 200, and 325. Other sieve sizes may of course be used depending on the characteristics of the particular soil sample being tested.

Each sieve is first weighed empty and placed on top of a receiver container in order of decreasing size. For example, in the array of sieves identified above, the No. 325 sieve would be on the bottom and the No. 10 sieve would be on the top.

The soil sample to be evaluated is weighed and placed on top of the uppermost sieve. The soil sample is then sprayed with water until no further fines removal through the sieve is observed. Next, the top sieve is removed and the next sieve is sprayed as previously until no further fines removal is observed. This procedure is repeated until all of the sieves have been adequately rinsed. The rinsed sieves are then weighed and dried in a hood or low temperature oven at about 50° C. After drying, the dried sieves are again weighed and the weight of dried soil sample contained on each sieve is determined.

All of the effluent water from the sieving process, that is, water containing solids of smaller particle size than are held by the smallest mesh sieve, in this case, less than 325 mesh solids, is filtered. This is accomplished in known fashion, for example, by weighing the filter paper, then weighing the filter paper plus the collected wet solids, drying the solids in a hood or low temperature oven, weighing the dry solids and weighing the filtrate. Care should be taken that the temperature of the drying does not drive off the more volatile organic contaminants.

Figure 3:
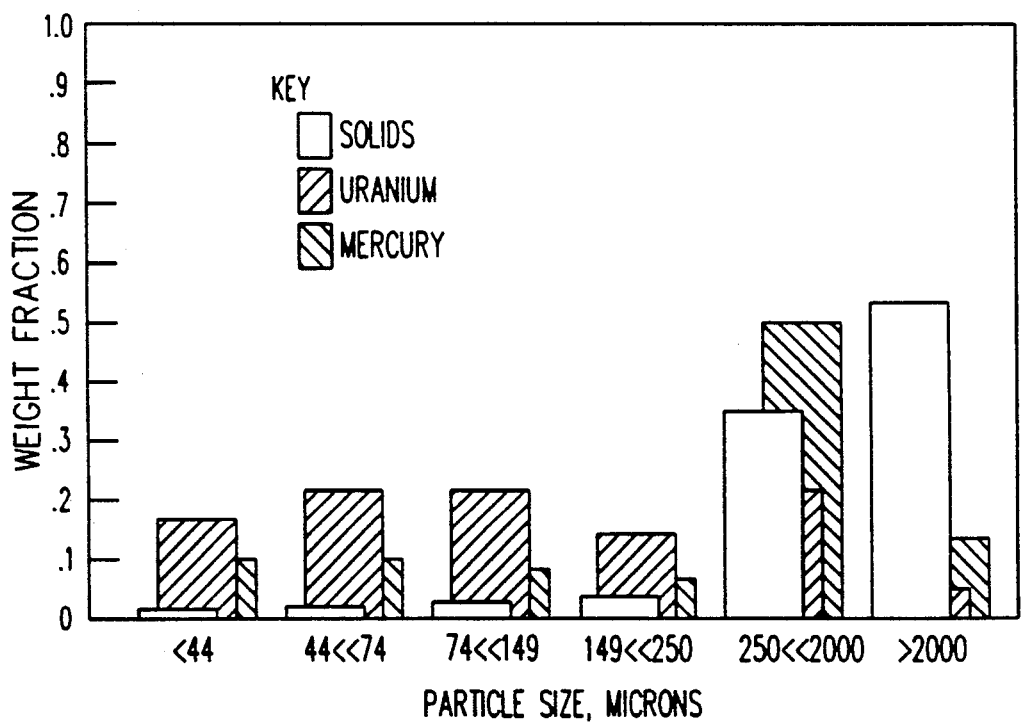
FIG. 3 is a graphical representation of contaminant concentration versus particle size distribution for a soil sample evaluated according to a preferred embodiment of the present invention.

After all of the dried solids are classified, including the dried filtrate, the solids are examined through analysis for contaminants of interest. In this way, it is possible to determine which contaminants are more heavily associated with which classification of soil sizes. The particular method of evaluating the dry solids for contaminants of interest is not critical, so long as it is tailored to the particular contaminants of interest and is suitable for analyzing dried solids. Examples of analysis procedures for determining contaminants of interest include, e.g., mass spectrometry, IR spectrometry, gas chromatography, or any other known analysis method. An example of the type of data generated by this procedure is shown in FIG. 3, which illustrates the correlation between particle size ranges and two contaminants of interest, mercury and uranium, for one soil sample.

The second phase of the process of the invention involves the identification of an effective extractant for use in connection with the particular soil of interest. In this phase of the process, extraction testing is used to determine the optimal conditions for removing the contaminants identified in the first step from the soil or soil fraction. Specifically, extractants testing is preferably performed on those size fractions of soil exhibiting levels of contamination above acceptable levels.

This second step examines the effects of extractant chemistry, extractant concentration, extractant solution-to-soil-weight ratio, and contact time on the efficiency of contaminant removal from the soil. In this regard, once contaminants of interest have been identified, it is possible to determine what extractants or combination of extractants could be used for extracting each contaminant. Ideally, the extractants are themselves relatively non-toxic, since in most cases they will reenter the site. For metals, the objective is generally to solubilize the metal with the extractant. For organics, the goal may also be to solubilize, e.g. with surfactants. In either case, the objective is to determine the lowest effective concentration of active extractant possible, to minimize the cost of the soil cleaning process. Thus, this second step may involve running a bench scale soil washing process on the same soil using the same extractant, but in different concentrations to determine the best economies of the soil washing system.

This step is carried out using equipment which mimics the soil washing process to be used on the full scale site. In the description immediately following, the specific procedures in this second step have been selected to mimic the soil washing process presented in FIG. 2. Of course, any soil washing process could benefit from the invention, and the scope of this invention should in no way be construed to be limited to a bench scale soil washing process that mimics the process of FIG. 2.

The equipment used in this step includes sieves such as those used in the first phase of the process just described, a balance such as a Fisher Scientific XT-3000 DR, and a food blender or bench attrition mill.

In initiating the second step, the appropriate sieves to be used are identified once again. As previously described, typical sieve sizes may include but are not limited to numbers 10, 20, 50, 100, 200 and 325. The particular sieves used will, of course, depend upon the actual soil being tested, the results of the wet screen contaminant identification described above in step 1 and the process being modeled. Each sieve size should be chosen to represent a point in the soil washing process where a major stream of material is to be removed from the process. Preferably, these points correlate to a range of particle sizes identified in the first step as bearing the most significant share of the contaminants of interest. In this particular embodiment, screens used include 1 inch, 48 mesh (297 micron) and 325 mesh (44 micron).

A known amount of the representative contaminated soil sample is placed on the largest sieve, which is positioned over a collection container. Preferably, this soil sample is selected from the same sample used to produce the particle size characteristics in step 1, however, preferably the soil used in step 1 is not reused in step 2. That is, preferably fresh contaminated soil having the same characteristics as the soil used in step 1 is used for step 2.

The soil sample is sprayed with a known amount of an extractant solution while sieving the sample vigorously. Examples of extractant solutions include, for example, leachants, surfactants, water, detergent solutions, oxidizing and reducing agents, etc. The type of extractant used depends upon the contaminants of interest, which contaminants are identified as set forth in step 1. After spraying the uppermost sieve with the known amount of extractant solution, the sieve is then sprayed with a known amount of rinse water, again, while sieving the sample vigorously. After the sieve is rinsed, it is removed from above the container, dried as previously described and weighed. The dried product remaining on the screen is then analyzed for the contaminant of interest.

The contents of the receiver container are placed into the blender or bench scale attrition mill/scrubber and processed for a predetermined amount of time, generally several minutes.

The next largest sieve is then placed on top of a receiver container, in this case, the 48 mesh sieve. The contents of the blender or bench scale scrubber are then poured over the 48 mesh screen which is sprayed with a known amount of rinse water while sieving vigorously. After the sieve is sufficiently rinsed, it is removed, dried as previously described and weighed to determine the amount of dried soil sample contained on the screen. This dried product is then analyzed for the contaminant of interest.

The contents of the receiver container are once again placed into the blender or bench scale scrubber and processed for a predetermined amount of time, generally several minutes. The next largest sieve, in this case the 325 mesh sieve, is then placed on the top of a receiver container and the contents of the blender or bench scale scrubber are poured onto this sieve. The effluent running through the screen is collected in the receiver container and placed into a storage container. The contents of this screen are then emptied into a blender or bench scale scrubber along with a known amount of extractant and processed for a predetermined amount of time, again, generally several minutes. The contents of the blender or scrubber or then poured once again onto the 325 mesh sieve which is sprayed with a known amount of rinse water while sieving vigorously. After the sieve has been rinsed, it is removed, dried and weighed as previously described and the dried product is analyzed for the contaminant of interest.

The above procedure is preferably repeated using at least one additional extractant to determine which extractants extract the greatest amount of contaminant of interest from the particular soil being studied. Also, different concentrations of the same extractants may be used to determine the lowest effective concentration for extraction of the contaminants of interest.

The third phase of the soil sample bench scale evaluation process involves the identification of an effective leachate treatment approach for the soil of interest. Removing contaminants from the soil requires that these liberated contaminants be treated, either for recycle or disposal. For example, heavy metal contaminants may be removed by flocculation and filtration. Organics may be pyrolized. As used herein, the term "leachate treatment" refers to all methods whereby contaminants, after removal from soils and as contained in leach solutions, fines and wash solutions, are rendered more environmentally acceptable, e.g., by fixing, e.g., in a concrete matrix, or smelting, in the case of metals, or pyrolizing, in the case of organics.

In this third phase, all wash solution, leachate and fines are tested to define a suitable treatment process. Various methods for treatment include pH adjustment, precipitation, flocculation and/or absorption. Precipitation methods include hydroxide or sulfide precipitation or water glass co-precipitation in the case of metal contaminants, and calcium chloride precipitation for organic contaminants.

Flocculation includes chemical or electrolytic flocculation and removal using mechanically aided devices or settling tanks.

Absorption media include ion exchange resins, zeolites, activated carbon and treated clays, for example.

The choice of specific treatment techniques selected depends on the type and level of the contaminants. In this example, it is assumed that the fines are contaminated and must be removed and dewatered. This is the situation facing the typical contaminated soil site. The extractant will be assumed to contain the solubilized contaminant which is a metal and which is removable on an ion exchange column. The equipment used in this phase includes a 500 ml. beaker, a 1 inch diameter by 18 inch high glass column, a pH meter, a pipette for adding reagents, and a variable speed laboratory stirrer.

In this phase of the process, a sample of fines slurry from the above step 2 is obtained and placed in the 500 ml. beaker. In this example, a 400 ml. sample of fines slurry was obtained. The pH of the fines slurry was adjusted to about 6.7 using HCl in order to precipitate humic materials. The amount of HCl added to achieve the desired pH is recorded. This pH adjusted solution is then analyzed for the concentration of the contaminant of interest.

While gently stirring with the laboratory stirrer, flocculent solution is then added to the 40 ml. sample until flocs form and material settles from the solution. The amount of floc solution added to obtain this settling is recorded. Additionally, the volume of settled floc formed is recorded. The settled slurry is then filtered.

Next, the filtrate is carefully poured onto the resin bed which has been filled with water to the top of the resin, and the resin bed is drained from the bottom until all of the filtrate has been processed.

The amount of resin required to absorb all of the metal contaminant is estimated. This estimated amount of resin is removed from the top of the column. Next, the resin which has been removed from the column is stripped with a known volume of regenerating solution and the concentration of the contaminant of interest in the regenerating solution is measured. The recovery of the contaminant by the regenerating solution compared to the amount of contaminant poured into the column from the filtrate is the removal efficiency for the resin column.

EXAMPLE 1

A soil contaminated with a mixture of mercury and uranium was tested. The soil washing process tested was substantially the same as that illustrated in FIG. 2. The results of the soil fraction/contaminant screening process are illustrated in FIG. 3. This information was used to develop the leachate system. Typical product results for the bench scale tests are shown in Table 1. Based on the success of the bench scale tests, a pilot test was carried out with about 50 pounds of soil using an actual attrition scrubber and a mineral jig. These results are shown in Table 2. There exists as illustrated a very good agreement in performance between the two tests shown in Tables 1 and 2.

Referring again to FIG. 3 it is clear that the 250 micron particle size represented a logical cut point for this particular soil sample since most of the uranium contamination occurred in particle sizes less than 250 microns while most of the mercury contamination occurred in the particle size fractions greater than 250 microns.

TABLE 1

Results of Bench Scale Treatability Test

| Particle Size Fraction | Treatment | Residual Soil Contaminant Levels | |
|---|---|---|---|
| | | Uranium | Mercury |
| <250 micron | Segregation by Sieving | 890 ppm | 4500 ppm |
| 250 << 200 micron | Batch Contact with 18g/l NaOCl, pH 6 | 30–45 ppm | 90–150 ppm |

TABLE 2

Results of Pilot Scale Treatability Test

| Treatment | Product Stream | Residual Soil Contaminant Levels | |
|---|---|---|---|
| | | Uranium | Mercury |
| Attrition scrub with 20g/l NaOCl, pH 6 followed by mineral jig | a) −250 micron | 735 ppm | 2000 ppm |
| | b) +250 micron | 20–50 ppm | 100–135 ppm |

EXAMPLE 2

In this example, soil contaminated with a mixture of gasoline, diesel oil and lead will be evaluated. The extractant to be used for this example is a commercial detergent, comprising a solution of NP90 (Henkel Corporation, Ambler, Pa. 19002) and Asee 799 (Witco Corporation, Houston, Tex. 77245) in water. The detergent solution is pH adjusted to about 12 with NaOH. A first detergent solution will include 1% of both NP90 and Asee 799. A second detergent will include 0.5% of both NP90 and Asee 799.

Use a sample splitter to remove a 500-gram aliquot of soil. This aliquot is wet-sieved into three fractions, >2 mm, 50 micron < <2 mm, and <50 micron.

The fractions larger than 2 mm are rinsed with water and the washed solids assayed for organics and lead.

Next, the 50 micron < <2 mm fraction is contacted with the first detergent solution in an attrition scrubber for about 20 seconds. The solids are then rinsed with water and resieved to the same three size fractions to estimate the extent of particle attrition. These solids are then assayed for the presence of organics and lead.

Next, the <50 micron fines are filtered from the combined wash (detergent) and rinse solutions collected from the previous steps. The solutions are treated with sodium oxalate followed by electrocoagulation, both with and without precipitation using $CaCl_2$, and the effluent is assayed for organics and lead.

The above procedures are then repeated using the second detergent solution.

During the bench scale treatment process of this example, the following samples are collected for assay for contaminants:

1. One sample from each of the three dry sieve sizes (before washing). (Total three samples.)
2. Two samples from each of the three wet sieve sizes for each wash solution used. (Total 12 samples.)
3. Three liquid samples, one before and one after treatment, without $CaCl_2$ and with $CaCl_2$ precipitation for each leachate. (Total 6 samples.)

I claim:

1. A method of characterizing contaminated soil and determining an effective treatment approach for removing contaminants from said soil, said method comprising the steps of:
   (a) obtaining a representative contaminated soil sample from a site containing said contaminated soil;
   (b) (i) identifying particle size ranges from said contaminated soil by passing at least a portion of said representative contaminated soil sample through a series of particle size classifying means and (ii) analyzing each size range of particles for contaminants of interest in order to correlate the levels of said contaminants of interest with said size ranges to determine which of said size ranges has a greater proportion of said contaminants than other particle size ranges;
   (c) utilizing the information with respect to particle size ranges and contaminants from step (b)(ii), identifying a first extractant to be used to remove said contaminants of interest from said contaminated soil by passing at least a portion of said representative contaminated soil sample containing size ranges determined to have a greater proportion of said contaminants through a first bench scale soil washing process adapted to substantially correspond to a full-scale soil washing process for said contaminated soil, said first bench scale soil washing process adapted for removing said contaminants from contaminated soils having particle size ranges corresponding to said ranges determined in step (b)(ii), said first bench scale soil washing process including washing a known quantity of said representative soil sample with said first extractant, analyzing said washed sample for the quantity of said contaminants of interest remaining on said washed sample and
   (d) repeating step (c) with a second bench scale soil washing process on at least one additional representative contaminated soil sample obtained from said site with a second extractant, comparing the quantity of said contaminants remaining on said washed soil following said second bench scale soil washing process with the quantity of said contaminants remaining on said washed soil following said first bench scale soil washing process in order to determine which of said first or second bench scale soil washing processes favors extraction of said contaminant from said contaminated soil; and
   (e) identifying a suitable leachate treatment process for treating contaminants removed in step (c) from said representative contaminated soil sample.

2. The method of claim 1 wherein said contaminants in said contaminated soil comprise heavy metals, radioactive compounds, organics, or a combination thereof.

3. The method of claim 1 wherein said particle size classifying means comprise a set of screens including a first screen and at least one additional screen, arranged in order of decreasing screen size relative to the direction of passing said representative contaminated soil sample through said screens.

4. The method of claim 3 wherein said screens comprise a range of sizes from No. 10 to No. 325.

5. The method of claim 3 wherein a known quantity of said representative contaminated soil sample is placed on said first screen and said first screen is rinsed with water to wash fines through said screen until no further fines removal is observed, and each successive said screen is rinsed with additional water until no further fines removal is observed, and step (b) further comprises the steps of:
   (a) drying any solids collected on said screens;
   (b) weighing said dried solids;
   (c) filtering all said rinse water to recover said fines;
   (d) drying said fines; and
   (e) analyzing said dried solids and fines for contaminants of interest.

6. The method of claim 1, wherein said bench scale soil washing process of step (c) comprises the steps of:
   (a) selecting a first particle classifying means capable of isolating a particle size from said representative contaminated soil sample corresponding to a size identified in step (b);
   (b) placing said particle classifying means in communication with a receiver means;
   (c) placing a known quantity of said representative contaminated soil sample on said first particle classifying means and spraying said sample with a known quantity of extractant solution;
   (d) rinsing said sample with a known amount of rinse solution comprising water or extractant solution while collecting a mixture of rinse solution and fines in said receiver means and collecting a first product sample in said first particle classifying means;
   (e) drying and weighing said collected first product sample;
   (f) analyzing said dried first product sample for a contaminant of interest;
   (g) processing said mixture of rinse solution and fines to extract at least one contaminant of interest from said fines;
   (h) passing said fines through a second particle classifying means while rinsing said fines with a known quantity of rinse solution and collecting a second mixture comprising fines and rinse solution, said second particle classifying means classifying a smaller size of fines than said first particle classifying means;
   (i) collecting a second product sample in said second particle classifying means and drying and weighing said second product sample;
   (j) analyzing said dried second product sample for a contaminant of interest.

7. The process of claim 1 wherein the treatment process of step (d) is performed on contaminant-bearing media selected from the group wash liquor, leachate, fines and mixtures thereof.

8. The process of claim 1 wherein the treatment process of step (d) is selected from the group pH adjustment, precipitation, flocculation, filtration, settling, absorption and combinations thereof.

9. The process of claim 6 wherein said first and second particle classifying means comprise screens for sieving said representative contaminated soil sample.

* * * * *